United States Patent [19]
Nakashima et al.

[11] Patent Number: 6,001,592
[45] Date of Patent: Dec. 14, 1999

[54] POLYPEPTIDE GENE CDNA, VECTOR CONTAINING SAID CDNA, HOST CELLS TRANSFORMED WITH SAID VECTOR, METHOD OF PRODUCING SAID POLYPEPTIDE, DNA ENCODING SAID POLYPEPTIDE

[75] Inventors: Kunio Nakashima; Shu Sudo, both of Mie-prefecture, Japan

[73] Assignee: Mikimoto Pharmaceutical Co., Ltd., Ise, Japan

[21] Appl. No.: 08/864,038

[22] Filed: May 28, 1997

[30] Foreign Application Priority Data

Jul. 15, 1996 [JP] Japan ................................. 8-184459

[51] Int. Cl.⁶ ............................ C12N 15/12; C12N 15/85
[52] U.S. Cl. ........................ 435/69.1; 435/91.1; 435/325; 435/348; 536/23.5
[58] Field of Search ............................... 435/69.1, 320.1, 435/243, 252.1, 91.1, 325, 348; 536/23.1, 23.5; 935/66, 60, 70, 72

[56] References Cited

PUBLICATIONS

C.M. Conduit and R.B. Meagher, Nature 323, 178–181, Sep. 11, 1986.

P.A. Guerette, D.G. Ginzigner, B.H. Weber, and J. M. Gosline, Science 272 (5258) 112–115, Apr. 5, 1996.

*Primary Examiner*—Julie Burke
*Attorney, Agent, or Firm*—Jordan and Hamburg LLP

[57] ABSTRACT cDNAs were synthesized from the mRNA isolated from the mantle epithelial tissue of pearl oyster (*Pinctada fucata*) using reverse transcriptase and joined to a vector to give a cDNA library. A cDNA inserted in this cDNA library was caused to be expressed in *Escherichia coli*, for instance, to give a polypeptide corresponding to said cDNA. This polypeptide serves as a novel ingredient of cosmetic compositions, for instance.

9 Claims, 1 Drawing Sheet

POLYPEPTIDE GENE CDNA, VECTOR CONTAINING SAID CDNA, HOST CELLS TRANSFORMED WITH SAID VECTOR, METHOD OF PRODUCING SAID POLYPEPTIDE, DNA ENCODING SAID POLYPEPTIDE

BACKGROUND OF THE INVENTION

1. Technical Field

The present invention relates to a gene cDNA for a novel polypeptide which is produced by the mantle tissue (mantle epithelial cells) of the Japanese pearl oyster (*Pinctada fucata*), a vector containing the cDNA, host cells transformed with the vector, a polypeptide produced thereby, a method of producing the same, a DNA coding for the polypeptide, an antibody to the polypeptide and a cosmetic composition containing the polypeptide or a degraded peptide derived therefrom.

2. Prior Art

In cases where it is desired to obtain a specific polypeptide or a DNA coding therefor, the prior art methods so far generally used identifies the desired polypeptide in a tissue or cell culture fluid, then isolates and purifies the polypeptide, and clones the gene or, alternatively, clones the gene through expression thereof using the presence of biological activity as an indicator.

However, the information concerning the factors produced by pearl oyster mantle epithelial cells is very scanty and the factors are mostly insoluble, making it difficult to isolate and purify them and identify them in terms of biological activity.

OBJECTS OF THE INVENTION

Generally, cells produce various factors involved in the maintenance, multiplication and growth thereof, among others. For example, pearl oyster mantle epithelial cells produce factors involved in shell formation or biophylaxis and many other factors.

Meanwhile, there have been rapid advances in the cDNA production and sequencing technologies, enabling rapid sequencing of a large number of cDNAs. There also have been marked advances in the methods of reverse genetics which uses a particular gene to fix the function thereof.

Directing their attention to these points, the present inventors made intensive investigations in an attempt to find out some novel factor (polypeptide) produced by certain cells (e.g. pearl oyster mantle epithelial cells). It is also an object of the present invention to develop a novel ingredient for cosmetic compositions or a novel method of piece selection (selecting pieces abundant in said polypeptide) in pearl culture.

SUMMARY OF THE INVENTION

The present inventors isolated mRNA from pearl oyster mantle epithelial cells, among others, obtained cDNA using the mRNA as a starting material, determined the nucleotide sequence thereof and deduced the encoded amino acid sequence. As a result, they succeeded in finding a DNA coding for a novel polypeptide and have now completed the present invention based on such finding.

Typical aspects of the present invention may be enumerated as follows:

A cDNA coding for the nucleotide sequence of SEQ ID NO:1.

A cDNA coding for the nucleotide sequence of SEQ ID NO:2.

A cloning vector containing the cDNA coding for the nucleotide sequence of SEQ ID NO: 1 or 2.

A DNA having the nucleotide sequence of SEQ ID NO:1 or a fragment capable of selectively hybridizing the sequence.

A DNA having the nucleotide sequence of SEQ ID NO:2 or a fragment capable of selectively hybridizing the sequence.

An expression vector containing the cDNA coding for the nucleotide sequence of SEQ ID NO: 1 or 2.

A bacterium, yeast, insect, insect cell, mammalian or other cell transformant harboring the expression vector.

A polypeptide produced by the transformant.

The polypeptide which has the amino acid sequence of SEQ ID NO:3.

A method of polypeptide production which comprises cultivating the transformant under conditions allowing the expression of the polypeptide.

An antibody prepared by using the polypeptide as an antigen.

A search was made for the DNA and polypeptide of the present invention among the known nucleotide sequences and amino acid sequences registered in the nucleotide sequence data base EMBL-GDB Rel. 41 and protein data base SWISS-PROT Rel. 30, respectively, but failed to identify any identical or homologous sequences. It was therefore confirmed that the DNA and polypeptide of the present invention are absolutely novel.

DETAILED DESCRIPTION OF THE INVENTION

First, mention is made of the polypeptides secreted by pearl oyster mantle epithelial cells. Each pearl oyster individual is externally covered with hard shells, which protect it from foreign enemies and the like. It is known that these shells, which perform a kind of biophylactic function, are made of mantle epithelial cells. The shells are mainly composed of crystalline calcium carbonate and a polypeptide. The pearl oyster shells have a structure comprising three distinguishable layers. These are called the shell epidermis (periostracal layer), ostracum (prismatic layer) and hypostracum (nacreous layer), from the exterior side. These structural differences are thought to be due to differences in the polypeptides.

The differences in polypeptides among the layers are, for the time being, ascribable only to differences in amino acid composition. This is because the polypeptides are mostly insoluble in water and in most other solvents, and this is a factor causing delays in analyzing those polypeptides.

Among these polypeptides, the hypostracum constituent polypeptide has been used since the days of antiquity as various remedies, for example as remedies for a cold, stomach diseases and so forth and is still in use in certain regions. It has been used also as an effective ingredient in cosmetics. The hypostracum of the shell structure is regarded as an equivalent to the pearl, which is widely appreciated as a jewel. The pearl is produced by about 1 to 3 years of cultivation of the pearl oyster following transplantation into the pearl oyster gonad of a spherical nucleus made of one of various shells, together with a piece, which is a pearl oyster mantle tissue section.

In view of the foregoing, it can be guessed that the polypeptides play a very important role in the decision of the color and the number and quality of nacre layers, which strongly influence the value of the pearl as a jewel.

The expression "DNA having the nucleotide sequence of SEQ ID NO:1 (or 2)" as used herein generally means a DNA at least 90%, for example 95%, 98% or 99%, of which has the nucleotide sequence of SEQ ID NO:1 (or 2). The term "fragment" as used herein with respect to such a homolog means a portion comprising at least 10 bases, preferably at least 15 bases, for example 20, 25, 30 or 40 bases. Such a fragment also falls under the category "DNA of the present invention" and can produce the same effects.

The expression "polypeptide encoded by a DNA having the nucleotide sequence of SEQ ID NO:1" or "polypeptide having the amino acid sequence of SEQ ID NO:3" generally means a polypeptide having an amino acid sequence at least 90%, for example 95%, 98% or 99%, of which is encoded by the DNA having the nucleotide sequence of SEQ ID NO:1. The term "fragment" as used herein with respect to such a homolog generally means a continuous region composed of at least 20, preferably at least 30, for example 40, 60 or 100, amino acid residues and having a degree of homology of at least 70%, preferably at least 80% or 90%, more preferably at least 95%. Any of such homologs, too, is hereinafter referred to as a polypeptide of the present invention (producing the same effects).

The DNA capable of selectively hybridizing the DNA having the nucleotide sequence of SEQ ID NO:1 or 2 is generally a continuous nucleotide sequence region comprising at least 20, preferably at least 30, for example 40, 60 or 100 bases and is homologous to an extent of at least 70%, preferably at least 80% or 90%, more preferably at least 95%. Such a DNA is also referred to as a DNA of the present invention, since it can produce the same effects.

The present invention further includes a cloning or expression vector containing the DNA of the present invention. As the vector, there may be mentioned, for example, plasmids, viruses, phage vectors and the like, which contain an ori region, if necessary a promoter for the expression of the DNA mentioned above, a promoter controlling element, etc. The vector may contain one or more selective marker genes, for example the ampicillin resistance gene. The vector can be used in vitro in producing an RNA corresponding to the DNA or in transforming host cells, for instance.

Furthermore, the present invention includes host cells transformed with a vector for the replication or expression of the DNA of the present invention which includes a DNA having the nucleotide sequence of SEQ ID NO:1 or 2 or the open reading frame thereof. As the cells, there may be mentioned, for example, bacteria, yeasts, insects, insect cells and mammalian cells.

The present invention further includes a method of producing the polypeptide of the present invention which comprises cultivating the host cells of the present invention under conditions enabling the expression of the polypeptide of the present invention. The cultivation is preferably carried out under conditions such that the polypeptide of the present invention is expressed and produced by the host cells.

The DNA of the present invention can be used in producing an antisense RNA by inserting said DNA into the antisense region of such a vector as mentioned above. Such antisense RNA can be used in controlling the intracellular level of the polypeptide of the present invention.

Furthermore, the use of the DNA of the present invention, a homolog thereof, or a fragment thereof as a probe for Northern analysis or as a primer for PCR (polymerase chain reaction) makes it possible to compare individuals with one another with respect to the level of expression of the polypeptide of the present invention.

The present invention still further includes a monoclonal or polyclonal antibody to the polypeptide of the present invention. Further, the present invention includes a method of producing such monoclonal or polyclonal antibody to the polypeptide of the present invention. The monoclonal antibody can be produced by conventional hybridoma technology using the polypeptide of the present invention or a fragment thereof as an antigen. The polyclonal antibody can be produced in the conventional manner by inoculating a host animal, for example a rat or rabbit, with the polypeptide of the present invention and recovering the serum.

The polypeptide of the present invention includes not only the one having the amino acid sequence of SEQ ID NO:3 but also modifications thereof derived by partial deletion, partial substitution of one or more different amino acids (e.g. amino acids having similar physical properties) and/or partial addition or insertion of one or more different amino acids.

As is well known, one to six codons are available for encoding one amino acid. Therefore, it is possible to modify the nucleotide sequence of a DNA without changing the amino acid sequence of a polypeptide.

The DNA of the present invention which is identified by SEQ ID NO:1 includes a group of all nucleotide sequences that code for the polypeptide identified by SEQ ID NO:3. Nucleotide sequence modification may sometimes lead to an improved productivity of the polypeptide.

The DNA of the present invention which is identified by SEQ ID NO:2 is an embodiment of the DNA identified by SEQ ID NO:1 and has a native-type sequence.

The DNA having the nucleotide sequence identified by SEQ ID NO:2 can be constructed by the following steps:

(I) Separating mRNA from the pearl oyster mantle tissue which is capable of producing the polypeptide of the present invention;

(II) Synthesizing a single-stranded DNA (first strand) based on said mRNA, followed by double-stranded DNA (second strand) synthesis (synthesis of cDNA);

(III) Incorporating the thus-obtained cDNA into an appropriate phage vector;

(IV) After packaging, infecting host cells with the infectious recombinant phage obtained (cDNA library construction);

(V) Screening the thus-obtained cDNA library using a specific probe; and (VI) Sequencing the clone obtained over the whole length thereof.

More detailedly, in step (I), the pearl oyster mantle is used as the starting material and the procedure of Chomczynski, P. et al. [Anal. Biochem., 162, 156 (1987)] is followed.

Steps (II), (III) and (IV) correspond to cDNA library construction steps and, essentially, the modified Gubler & Hoffman method [Gene, 25, 263 (1983)] is followed. Many are known as the phage vector to be used in step (III) (for example λgt10, λgt11). The term "phage vector" as used herein also includes phragemids, namely phage vectors convertible to plasmids by infection with helper phages.

In step (V), the relevant procedure described in Molecular Cloning [Sambrook, J., Fritsch, E. F., and Maniatis, T, Cold Spring Harbor Laboratory Press (1989)] is followed.

In step (VI), sequencing is performed by the Maxam-Gilbert method or dideoxy terminator method.

It is necessary for the thus-obtained DNA to be checked by: (A) converting its nucleotide sequence, in a possible reading frame thereof, to the corresponding amino acid sequence; (B) drawing a hydrophobicity profile based on the amino acid sequence obtained and further confirming the presence of a highly hydrophobic region immediately following the initiation codon (ATG) (secretory proteins have, at the N terminus thereof, a signal peptide which is a highly hydrophobic region); and, further, (C) confirming that said DNA covers the full length or nearly the full length.

In the above check procedure, the confirmation (C) can be obtained by Northern analysis. Once the nucleotide sequence of SEQ ID NO:1 or 2 has been confirmed, the DNA of the present invention can be obtained by chemical synthesis, by the PCR (polymerase chain reaction) method, or by hybridization using a fragment of said nucleotide sequence as a probe. Furthermore, the DNA of the present invention can be obtained in desired amounts by introducing a vector containing the DNA of the present invention into an appropriate host and multiplying the same.

The method of obtaining the polypeptide of the present invention includes (1) the method comprising isolating and purifying it from a living organism or cultured cells, (2) the method comprising peptide synthesis, and (3) the method comprising using recombinant DNA technology, among others. For commercial production, however, method (3) is preferred.

As the expression system (host-vector system) for polypeptide production using recombinant DNA technology, there may be mentioned expression systems comprising bacteria, yeasts, insects, insect cells and mammalian cells.

In the case of causing expression in *Escherichia coli*, for instance, an expression vector is constructed by joining the DNA having the nucleotide sequence of SEQ ID NO:1 downstream to an appropriate promoter (e.g. trp promoter, lac promoter, λPL promoter, T7 promoter), followed by insertion into a vector capable of functioning in *Escherichia coli* (e.g. pBR322, pUC18, pUC19). Alternatively, an expression vector may also be constructed by joining the DNA defined by SEQ ID NO:1 to a commercial expression vector (e.g. pKK223-3, Pharmacia; pET vector, Stratagene; pTV vector, Takara).

The *Escherichia coli* strain to be used includes, but is not limited to, *E. coli* JM109, *E. coli* HB101 and *E. coli* DH5, among others.

Then, an *Escherichia coli* strain transformed with said expression vector is cultivated in an appropriate medium. The desired polypeptide can be obtained from the thus-obtained cells. When use is made of a bacterial signal peptide (e.g. pelB signal peptide), the desired polypeptide can be secreted into the periplasm. Furthermore, it is also possible to obtain the desired polypeptide following production of a fusion protein thereof with an other appropriate polypeptide.

In the case of expression in an insect or in insect cells, a transfer vector is constructed, for instance, by inserting the DNA defined by SEQ ID NO:1 or 2 into an appropriate vector. Then, a recombinant virus is produced by cotransfection with a vector having the promoter of baculovirus (Autographa california NPV). The thus-obtained recombinant virus is introduced into appropriate insect cells (e.g. Sf9, Sf21 or Tn5 cells) or into the insect body (e.g. silkworm), whereby the desired polypeptide is produced.

In the case of expression in mammalian cells, an expression vector is constructed, for example, by inserting the DNA defined by SEQ ID NO:1 or 2 into an appropriate vector (e.g. retrovirus vector, papilloma virus vector, vaccinia virus vector, SV40 system vector) downstream from the promoter (e.g. SV40 promoter, LTR promoter, metal-lothionein promoter). Then, appropriate mammalian cells (e.g. simian COS cells, Chinese hamster CHO cells, mouse L cells) are transformed with the expression vector obtained and the transformant is cultivated in an appropriate medium. The desired polypeptide is produced in the transformant cells. The polypeptide produced in the above manner can be isolated and purified by conventional biochemical methods.

The polypeptide of the present invention can be applied as an ingredient in cosmetics. Thus, the polypeptide of the present invention can be admixed with other ingredients in common use to give a cosmetic composition. Further, by using the PCR method, for instance, it is also possible to develop a novel method of piece selection (selecting pieces abundant in said polypeptide) in pearl cultivation.

PREFERRED EMBODIMENTS OF THE INVENTION

Figure 1:
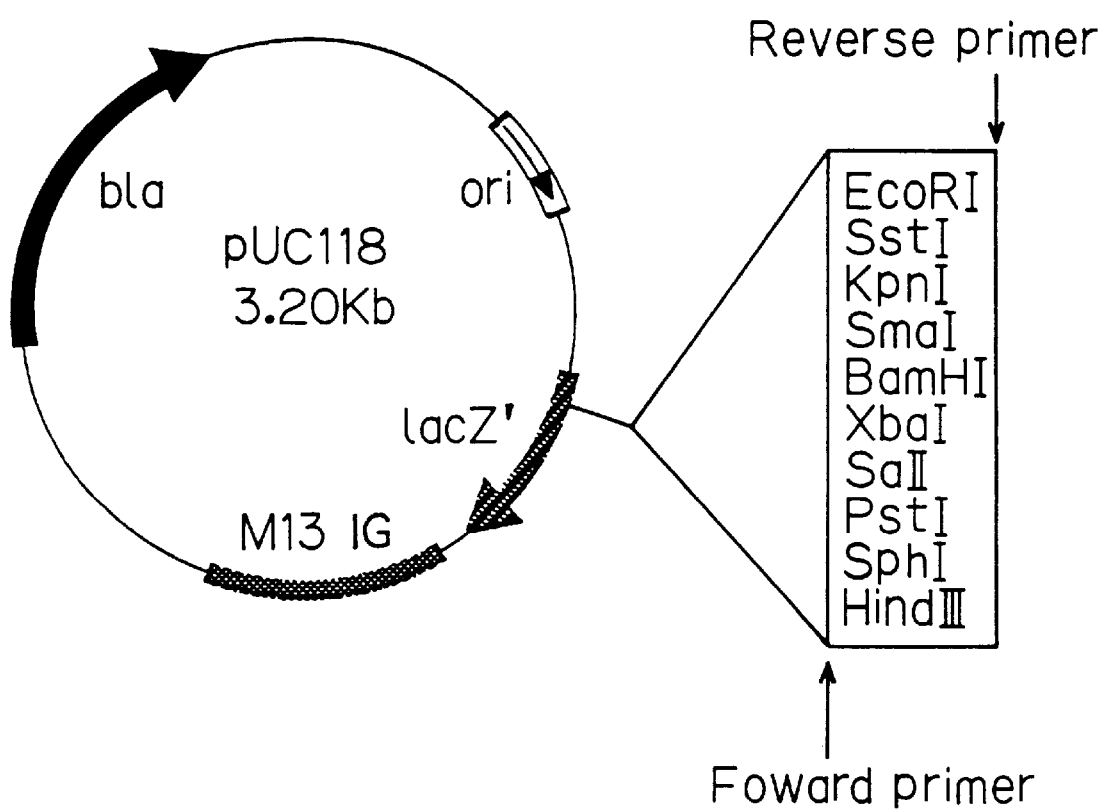
FIG. 1 is a schematic representation of the construction of an example of the cloning vector of the present invention.

The following examples illustrate the present invention in further detail. They are, however, by no means limitative of the scope of the present invention.

Example 1 (mRNA Separation and Purification)

Mantle epithelial cells (about 3 g) of pearl oyster (*Pinctada fucata*) were used and the total RNA was separated by the method of Chomczynski, P. et al. [Anal. Biochem., 162, 156 (1987)]. Today, the pearl oyster is readily available in Japan and other countries. Mantle epithelial cells of this organism are unfit for cryopreservation. No other adequate methods of preservation or adequate preservation conditions (medium etc.) have yet been found. Therefore, for the time being, they cannot survive (as cells) in isolated conditions. For this reason, the Agency of Industrial Science and Technology National Institute of Bioscience and Human Technology Patent-Related Microorganisms Deposition Center (Japan) refused to accept said cells as a deposit but issued a certificate of refusal to accept as deposit (discriminatory designation: *P. fucata* M01). The deposition of the pearl oyster itself was also refused. Said pearl oyster *Pictada fucata* has been preserved by the applicant himself and is ready for distribution.

Thus, The tissue was homogenized in 4 M GTC solution (4 M guanidine thiocyanate, 25 mM sodium citrate, 0.5% Sarcosyl, 0.1 M 2-mercaptoethanol). The homogenate was subjected to two phenol/chloroform extractions, followed by addition of isopropyl alcohol to the extract and centrifugation (10,000 ×g, 10 minutes). About 200 μg of total RNA was recovered in the sediment. From this, mRNA was further separated using oligo(dT) latex particles (obtained from Takara Shuzo). Thus was purified and recovered 2.5 μg of poly(A)+RNA.

Example 2 (Construction of a cDNA Library)

A modification of the Gubler and Hoffman method [described in Gene, 25, 263 (1983)] was used for the cDNA library construction.

Thus, starting with the poly(A)+RNA (2.5 μg) separated and purified in Example 1, single-stranded DNA (first strand) synthesis was performed using random hexamer and oligo(dT) primers in the presence of reverse transcriptase, followed by double-stranded DNA (second strand) synthesis. Then, the unreacted primers and RNA were removed by gel filtration column chromatography, and EcoRI adapter ligation was carried out. The unreacted adapter was removed again by gel filtration column chromatography, and a cDNA fraction was recovered.

The above step of cDNA synthesis was performed using the Time Saver cDNA synthesis kit (obtained from Pharmacia).

The cDNA fraction obtained above was subjected to ligation to the λgt10 phage vector, and packaging was performed using LAMBDA IN (in vitro packaging kit obtained from Nippon Gene). After titer confirmation by the usual technique, there was obtained a cDNA library with an independent clone number of $5.5 \times 10^5$ pfu.

Example 3 (Cloning)

Starting with the cDNA library obtained in Example 2 and using an LB plate (10 cm×14 cm), the pfu density was adjusted to about 10,000 pfu/plate. Separately, based on the data already available to the present inventors, a 20 mer synthetic nucleotide was prepared by entrusting Biologica with the synthesis thereof and isotope-labeled using [λ-$^{32}$P] adenosine-triphosphate and T4 polynucleotide kinase to give a labeled probe. Then, screening was conducted by plaque hybridization according to the method described in Molecular Cloning [Sambrook, J., Fritsch, E. F. and Maniatis, T., Cold Spring Harbor Laboratory Press (1989)], whereby a number of positive clones were obtained.

Example 4 (Clone Analyis)

Further, the DNA of each phage clone obtained was cleaved with the restriction enzyme EcoRI. Using one of the resulting fragments as a probe, Southern blot hybridization was carried out in the conventional manner. As a result, 8 clones out of 12 clones were found to be identical with one another. Three of the nonidentical four clones were of the same length while the remaining one clone (clone C2–5) was larger.

The cDNA library mentioned above was further screened using said clone C2–5 as a probe, giving three positive clones. These clones were each subcloned into the pUC118 plasmid vector at the EcoRI site thereof, followed by plasmid DNA separation and purification by the conventional method.

The thus-obtained clone C2–5 was subjected to Northern blot analysis. Thus, the total RNA extracted from each pearl oyster tissue was subjected to agarose gel electrophoresis, followed by blotting onto a nylon membrane. Hybridization using the cDNA insert of C2–5 as a probe revealed an expression band at the position corresponding to about 3,500 bases which was specific to the mantle alone.

Example 5 (Sequencing)

Since the plasmid has the structure shown in FIG. 1, sequencing was carried out using M13 forward and reverse primers. This enables reading of the nucleotide sequence from the 5' end and from the 3' end of the cloned cDNA. For reading of the internal portion of the cDNA, deletion clones were prepared in the conventional manner. DNA sequencing was performed using the BcaBEST dideoxy sequencing kit (obtained from Takara Shuzo) based on the dideoxy terminator method of Sanger, F. et al.

Editing of the thus-obtained sequence data was performed using the GENETYX DNA sequence linking program to give a continuous sequence. The nucleotide sequence disclosed in SEQ ID NO:2 was thus obtained. From this full-length cDNA sequence data, the open reading frame was determined and further translated into the corresponding amino acid sequence, which is disclosed SEQ ID NO:3.

The entire nucleotide sequence of the cDNA and the primary amino acid sequence of the protein encoded by the cDNA are diclosed in the sequence listing as SEQ ID NO:4.

Example 6 (Construction of Full-length cDNA)

Based on the sequencing results obtained in Example 5 and starting with two positive clones and utilizing the SacI cleavage site, the full-length C2–5 protein cDNA was constructed in the pUC118 vector.

An *Escherichia coli* strain (*E. coli* JM109) was transformed with the thus-constructed cloning vector. The transformant has been deposited with the Agency of Industrial Science and Technology National Institute of Bioscience and Human Technology Patent-Related Micro-organisms Deposition Center (discriminatory designation: *E. coli* MK002; international deposition number: FERM BP-5937).

Example 7 (Transformant Production)

The pUC118 plasmid vector with the C2–5 protein cDNA subcloned therein in Example 6 was cleaved with EcoRI and SalI and the thus-prepared C2–5 protein cDNA was inserted into the expression plasmid pGEX-5X-1 (obtained from Pharmacia). This expression vector was introduced into *Escherichia coli* JM109 to yield an appropriate transformant.

Example 8 (Polypeptide Production)

The transformant obtained in Example 7 was cultivated in one liter of ampicillin-containing L broth until the absorbance reached 0.6. Then, IPTG was added to a concentration of 0.5 mM and cultivation was further continued for 7 hours.

Then, cells were harvested and sonicated. The supernatant deprived of the cell debris was mixed with Glutathione-Sepharose (obtained from Pharmacia) and, after washing of Glutathione-Sepharose with phosphate buffer, the C2–5 protein was eluted with phosphate buffer containing 5 mM glutathione. This protein was dialyzed against phosphate buffer. Analysis of a portion of the dialyzate by SDS-polyacrylamide gel electrophoresis revealed that the GST-fused protein had been synthesized with a purity of at least 90%.

Example 9 (Antibody Production)

A rabbit was subcutaneously inoculated three times at 2-week intervals with the C2–5 protein purified in Example 8, together with complete Freund's adjuvant. Thereafter, the serum was collected.

Testing of this serum by Western blotting confirmed that it can be used as an antibody against the C2–5 protein even at a dilution level of about 1,000 times.

We claim:

1. An isolated cDNA consisting of the sequence of SEQ ID NO:1.

2. An isolated cDNA consisting of the sequence of SEQ ID NO:2.

3. A cloning vector containing the cDNA of claim 1 or 2.

4. An expression vector containing the cDNA of claim 1 or 2.

5. A bacterium, yeast, insect cell or mammalian cell transformant harboring the expression vector of claim 4.

6. A method of polypeptide production comprising cultivating a bacterium, yeast, insect cell or mammalian cell transformant harboring an expression vector containing a cDNA consisting of the sequence of SEQ ID NO:1 and producing the polypeptide from said transformant.

7. The method of polypeptide production according to claim 6, wherein the polypeptide consists of the amino acid sequence of SEQ ID NO:3.

8. A method of polypeptide production comprising cultivating a bacterium, yeast, insect cell or mammalian cell transformant harboring an expression vector containing a cDNA consisting of the sequence of SEQ ID NO:2 and producing the polypeptide from said transformant.

9. The method of polypeptide production according to claim 8, wherein the polypeptide consists of the amino acid sequence of SEQ ID NO:3.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
    (A) LENGTH: 2214
    (B) TYPE: nucleic acid
    (C) STRANDEDNESS: double
    (D) TOPOLOGY: linear (vi) ORIGINAL SOURCE:
    (A) ORGANISM: Pinctada fucata
    (G) CELL TYPE: mantle epithelial cell (xi) SEQUENCE DESCRIPTION: SEQ ID NO:1:

```
ATGAAGTTAC TGGTGGTTCT CACCACCCTC GTGGGCTTTA GCTCAGCACT AAGTTTCGGT      60

TGTAATTACA GACCAGTATT AGGCTTCAAT TCACAGTATA TGCTGGGAGG ACTAAGACTT     120

TTCTGTATGC CTGCCATGGT TTATGATCCA TGGGCATGTG GTTGCGTTTC GGCATGGAGC     180

AGTGCAGGTC TTTACGGTGT CGGAGGGGGC GGAGGCGCCT GGGGAGCTGG CGGTGCTGGA     240

GGAGCCGACG GCGGACGCGG CGGCGGCGGT GGAGATTGGG AATATGACTA TGATGACGAC     300

AGCGATGACG ATGATGAATG GGACTGGGAT GATGACGGTG GAATGGGAGC TGGCGCCGGA     360

GGTGGTGCTG GTGGTGGTGC CGGAGGTGGT GCTGGTGCTG GTGCTGGAGC AGGCGCAGGA     420

GCAGGAGCAG GTGCTGGACT CGGACTTGGA TTGGGCGGAG GTCTCGGAGG TGGACTTGGC     480

GGACTTGGAG GTCTTGGCGG ACTTGGCGGT GGAGACGATT TATTTGATTT AGATTTCGAT     540

GATCTTGGTG CAGCTCTTGC CCTCGGTGGA GCTGGTGGAG CTGGAGGTGC TGCTGCTGCT     600

GCTGCAGCTG CCGCTGCTGC CGCCGGGGGT GGAGTTGGTG GAGCTGCTGC CGCAGCCGCA     660

GCCGCTGCTG CCGCTGCAGG AGGAGGCGCA GGTAGACTTG GAGGAGCTGC TGCTGCAGCC     720

GCAGCCGCTG CTGCCGCTGC AGGAGGCGCA GGTGGACTTG GAGGACTCGG TGGCGGACTT     780

GGAGGACTCG GTGGCGGACT TGGAGGCCTC GGAGGTCTTG GTGGCCTCGG AGGATATGGA     840

GGATCTGCTG CTGCCGCTGC TGCTGCTGCC GCCGCTGCTG CCGGAGGTGG AGGACTCGGT     900

GGTGTTGGTT CTACGGTGG ACGAGGAGGT AGACGCGGTC GAGGAAGAGG AGGCCGCAGA     960

CGTGCTGCTG CTGCCGCTGC TGCAGCTGCC GCCGCAGCCG CTGGTGGTGG CGGAGGAGGT    1020

GGAGGTGGTG GAGGAGGAGG CGGAGGCGCT GGTGCTGCCG CTGCCGCTGC AGCCGCTGCT    1080

GCATCTGCTT CAGCTTCTAG ACAAATGAGT GGTATAAGGG ACGCATTAGG AGACATTAAA    1140

GACCTTCTCA GGAGTAATGG AGCCTCTGCA AAAGCCTCTG CTAAAGCATC AGCAGTAGCA    1200

AGCACAAAAT CTCAAATTGA CGATTTGAAG GATGTCTTAA AGGATCTTGC AGGTCTATTG    1260

AAAAGCTCAG CATCTGCTTC AGCATCTGCA TCTGCATCAG CTTCAGCTGG AGGTGGAGGC    1320

GGTGGTGGTA ACGGAGGTGG TAACGGAGGA GGAGGCGGCG GTGGAGCTGG AGCTCTAGCT    1380

GCTGCTCTCG CTGCTGCAGG AGCCGGAGGT GGACTTGGAG GTGGAGGCGG AGGCGGAGCT    1440

TTAGCCGCTG CACTAGCTGC TGCTGGTGCA GGTGGAGGAG GTTTTGGTGG ACTTGGAGGA    1500

CTAGGCGGTC TTGGTGGGGG ATCTGCCGCA GCTGCTGCAG CCGCTGCCGC TGCTGCATCA    1560

GGTGGTGGAG GAAGAGCACT TAGAAGGGCT TTGAGAAGAC AAATGCGTGG AGGTGGATCC    1620

GCTGCTGCCG CTGCTGCTGC TGCTGCAGCT GCTGCTGGAG GTGGATGGGG AGGTGGAATG    1680

GGTGGAGGAT TCGGAGTAGG TCTCGGTGGA GGATTCGGAG GAGGATTTGG TGGTGGATCA    1740

TCAGCAGCAG CTGCTGCCGC TGCTGCAGCC GCCGCTGGAT TTGGTGGAGG TGGACGAAGA    1800

GGTAGAGGTA GAGGACGTGG AGGCGATGGC GACGGTAACG GAGCTAGTGC TGTAGCTGCA    1860

GCCGCCGCCG CTGCTGCTGC TGCTGGAGGA TCTGCTGCTG ATGTTGCCGC TGCCGCTGCT    1920

GCAGCCGCAG CTATGTACGG TGACGGTGCT GATGGACCTG ATTTCGATAA TGGATTCGGT    1980

GGTGGAAACG GAAATGGAGG TGGCGGATCT GGTGGTGGCG GATCCGGCGG AGGTGGATCC    2040
```

```
GGTGGCGGAT CTGGAGGTGG CGGTGGATCT GGTGGATCAG GCGGTGGCGG CGGATCTGGT    2100

GGTTCAGGCG GTGGCGGATC AGGCGGCGGT GGAAACAATG GATGGGGAAA TAACGGCAAC    2160

AATAAATATG ACGATGATGA CTGTGATGAA TATGGTAACC CTATTAGAAG GGGG          2214

(2) INFORMATION FOR SEQ ID NO: 2:

(i) SEQUENCE CHARACTERISTICS:
        (A) LENGTH: 3331
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Pinctada fucata
        (G) CELL TYPE: mantle epithelial cell (ix) FEATURE: mRNA
        (B) LOCATION: from 1 to 3331
        (C) IDENTIFICATION METHOD: E (by experiment)

(xi) SEQUENCE DESCRIPTION: SEQ ID NO:2:

TCGGATCTCC CCACACAACA TAGATAGAGG ATATCCGCCT GGGTTCACAA TGAAGTTACT      60

GGTGGTTCTC ACCACCCTCG TGGGCTTTAG CTCAGCACTA AGTTTCGGTT GTAATTACAG     120

ACCAGTATTA GGCTTCAATT CACAGTATAT GCTGGGAGGA CTAAGACTTT TCTGTATGCC     180

TGCCATGGTT TATGATCCAT GGGCATGTGG TTGCGTTTCG GCATGGAGCA GTGCAGGTCT     240

TTACGGTGTC GGAGGGGGCG GAGGCGCCTG GGGAGCTGGC GGTGCTGGAG GAGCCGACGG     300

CGGACGCGGC GGCGGCGGTG GAGATTGGGA ATATGACTAT GATGACGACA GCGATGACGA     360

TGATGAATGG GACTGGGATG ATGACGGTGG AATGGGAGCT GGCGCCGGAG GTGGTGCTGG     420

TGGTGGTGCC GGAGGTGGTG CTGGTGCTGG TGCTGGAGCA GGCGCAGGAG CAGGAGCAGG     480

TGCTGGACTC GGACTTGGAT TGGGCGGAGG TCTCGGAGGT GGACTTGGCG GACTTGGAGG     540

TCTTGGCGGA CTTGGCGGTG GAGACGATTT ATTTGATTTA GATTTCGATG ATCTTGGTGC     600

AGCTCTTGCC CTCGGTGGAG CTGGTGGAGC TGGAGGTGCT GCTGCTGCTG CTGCAGCTGC     660

CGCTGCTGCC GCCGGGGGTG GAGTTGGTGG AGCTGCTGCC GCAGCCGCAG CCGCTGCTGC     720

CGCTGCAGGA GGAGGCGCAG GTAGACTTGG AGGAGCTGCT GCTGCAGCCG CAGCCGCTGC     780

TGCCGCTGCA GGAGGCGCAG GTGGACTTGG AGGACTCGGT GGCGGACTTG GAGGACTCGG     840

TGGCGGACTT GGAGGCCTCG GAGGTCTTGG TGGCCTCGGA GGATATGGAG GATCTGCTGC     900

TGCCGCTGCT GCTGCTGCCG CCGCTGCTGC CGGAGGTGGA GGACTCGGTG GTGTTGGTTT     960

CTACGGTGGA CGAGGAGGTA GACGCGGTCG AGGAAGAGGA GGCCGCAGAC GTGCTGCTGC    1020

TGCCGCTGCT GCAGCTGCCG CCGCAGCCGC TGGTGGTGGC GGAGGAGGTG GAGGTGGTGG    1080

AGGAGGAGGC GGAGGCGCTG GTGCTGCCGC TGCCGCTGCA GCCGCTGCTG CATCTGCTTC    1140

AGCTTCTAGA CAAATGAGTG GTATAAGGGA CGCATTAGGA GACATTAAAG ACCTTCTCAG    1200

GAGTAATGGA GCCTCTGCAA AAGCCTCTGC TAAAGCATCA GCAGTAGCAA GCACAAAATC    1260

TCAAATTGAC GATTTGAAGG ATGTCTTAAA GGATCTTGCA GGTCTATTGA AAAGCTCAGC    1320

ATCTGCTTCA GCATCTGCAT CTGCATCAGC TTCAGCTGGA GGTGGAGGCG GTGGTGGTAA    1380

CGGAGGTGGT AACGGAGGAG GAGGCGGCGG TGGAGCTGGA GCTCTAGCTG CTGCTCTCGC    1440

TGCTGCAGGA GCCGGAGGTG GACTTGGAGG TGGAGGCGGA GGCGGAGCTT TAGCCGCTGC    1500

ACTAGCTGCT GCTGGTGCAG GTGGAGGAGG TTTTGGTGGA CTTGGAGGAC TAGGCGGTCT    1560
```

```
TGGTGGGGGA TCTGCCGCAG CTGCTGCAGC CGCTGCCGCT GCTGCATCAG GTGGTGGAGG    1620

AAGAGCACTT AGAAGGGCTT TGAGAAGACA AATGCGTGGA GGTGGATCCG CTGCTGCCGC    1680

TGCTGCTGCT GCTGCAGCTG CTGCTGGAGG TGGATGGGGA GGTGGAATGG GTGGAGGATT    1740

CGGAGTAGGT CTCGGTGGAG GATTCGGAGG AGGATTTGGT GGTGGATCAT CAGCAGCAGC    1800

TGCTGCCGCT GCTGCAGCCG CCGCTGGATT TGGTGGAGGT GGACGAAGAG GTAGAGGTAG    1860

AGGACGTGGA GGCGATGGCG ACGGTAACGG AGCTAGTGCT GTAGCTGCAG CCGCCGCCGC    1920

TGCTGCTGCT GCTGGAGGAT CTGCTGCTGA TGTTGCCGCT GCCGCTGCTG CAGCCGCAGC    1980

TATGTACGGT GACGGTGCTG ATGGACCTGA TTTCGATAAT GGATTCGGTG GTGGAAACGG    2040

AAATGGAGGT GGCGGATCTG GTGGTGGCGG ATCCGGCGGA GGTGGATCCG GTGGCGGATC    2100

TGGAGGTGGC GGTGGATCTG GTGGATCAGG CGGTGGCGGC GGATCTGGTG GTTCAGGCGG    2160

TGGCGGATCA GGCGGCGGTG GAAACAATGG ATGGGGAAAA AACGGCAACA ATAAATATGA    2220

CGATGATGAC TGTGATGAAT ATGGTAACCC TATTAGAAGG GGGTAAATTA TTTGACATTA    2280

TCCGCCATTT GACTCATTTT TCTTAGTTCT CTATGTTTTA TACTTCACCT TAGATTGTTT    2340

TAGTTTGATT GAATAAATTA TGTTTTCGAT ATAAATTTTT TTTAAATTAA ATTAAACTTT    2400

ATTAGTTGAC CTGTAAACTT TTTCATGGAG TTATAATCTA AGGAACAAAA AACATACATA    2460

ATATGTTCAG TATTGTGGTA AAGCACCTGT ACCGCAAACA CAATCACCTC TATACATGTA    2520

TACAAAATCA GTAATGCTGA CAAAATCTTC TACACTCTCA CCTACACACT CGCACACAGT    2580

CCTCTTACAT ACACAGCACT ATAATATCCT GAACATGAAG TTTGTGTTGA TAAAAAGTTC    2640

AGAAAAATCT CCCCTACATC ACCTGATCTT TCACTGAAAA TTTACGACAA GTATTGAAAA    2700

TAGCAGAAAG AAAACGGGAA ATTGAGAAGT TTTCTATAAA AAACAATCGG AACAATGACT    2760

GGAATGACAA GGATGAAAAT AATGATAACT TACATTAATT AAGGCCCCAA TAATCTCTCT    2820

ATTTTCAAAC TTTTTTTTCA AATGTTCTCT CTAACTCACT TGCATCTATG TGGAAATTCA    2880

CATACTATAC TAAATTACCA CAAGTATCAA GGTTTCACAA CCTCTCATGC CTTCATGGCA    2940

GACCATGCTG GGTATTTGTC TAACAATGCC TCATAAATAC ATAAAACTAA CTAACAAAAT    3000

AGGTCAGTCT GTAACAAATT ATTAATGCAC CATTATTGCA TTTTCTAAAA CAAAGCATAC    3060

ACTGGATATT GGCAGACAAA ATGTTGTTAT TGGATACCTT TCCATTCTAT CTAGACACTT    3120

GCTTTCCACA AGTCATCATA AATAAATCCC CCCTATCCCA AATGTCAATG GAATGCCCCA    3180

ACCCTTCCCC CATAATTTTA AAACCTAGAA TAAATTAAAA CATCTATAGT TCGTCATGAT    3240

CATCTTTCTT ATCATCCTCT TCTTCTTCCT CCTCCTCCTT CTTCTTCTTC CTCCTCCTCA    3300

GGTTCTTGGC TGCCTGCTCC TTCCTTGCCA A                                   3331
```

(2) INFORMATION FOR SEQ ID NO: 3:

(i) SEQUENCE CHARACTERISTICS:
        (A) LENGTH: 738
        (B) TYPE: amino acid
        (D) TOPOLOGY: linear (ii) MOLECULE TYPE: protein (vi) ORIGINAL SOURCE:
        (A) ORGANISM: Pinctada fucata
        (G) CELL TYPE: mantle epithelial cell (ix) FEATURE:
        (A) NAME/KEY: peptide
        (B) LOCATION: from 1 to 738
        (C) IDENTIFICATION METHOD: E (by experiment)

(xi) SEQUENCE DESCRIPTION: SEQ ID NO:3:

-continued

```
Met Lys Leu Leu Val Val Leu Thr Thr Leu Val Gly Phe Ser Ser Ala
 1               5                  10                  15

Leu Ser Phe Gly Cys Asn Tyr Arg Pro Val Leu Gly Phe Asn Ser Gln
            20                  25                  30

Tyr Met Leu Gly Gly Leu Arg Leu Phe Cys Met Pro Ala Met Val Tyr
        35                  40                  45

Asp Pro Trp Ala Cys Gly Cys Val Ser Ala Trp Ser Ser Ala Gly Leu
    50                  55                  60

Tyr Gly Val Gly Gly Gly Gly Ala Trp Ala Gly Gly Ala Gly
 65              70                  75                  80

Gly Ala Asp Gly Gly Arg Gly Gly Gly Gly Asp Trp Glu Tyr Asp
            85                  90                  95

Tyr Asp Asp Asp Ser Asp Asp Asp Glu Trp Asp Trp Asp Asp Asp
                100                 105                 110

Gly Gly Met Gly Ala Gly Ala Gly Gly Ala Gly Gly Gly Ala Gly
            115                 120                 125

Gly Gly Ala Gly Ala Gly Ala Gly Ala Gly Ala Gly Ala Gly
        130                 135                 140

Ala Gly Leu Gly Leu Gly Leu Gly Gly Leu Gly Gly Leu Gly
145                 150                 155                 160

Gly Leu Gly Gly Leu Gly Gly Leu Gly Gly Gly Asp Asp Leu Phe Asp
                165                 170                 175

Leu Asp Phe Asp Asp Leu Gly Ala Ala Leu Ala Leu Gly Gly Ala Gly
            180                 185                 190

Gly Ala Gly Gly Ala Ala Ala Ala Ala Ala Ala Ala Ala Ala
        195                 200                 205

Gly Gly Gly Val Gly Gly Ala Ala Ala Ala Ala Ala Ala Ala
        210                 215                 220

Ala Ala Gly Gly Gly Ala Gly Arg Leu Gly Gly Ala Ala Ala Ala
225                 230                 235                 240

Ala Ala Ala Ala Ala Ala Ala Gly Gly Ala Gly Gly Leu Gly Gly Leu
                245                 250                 255

Gly Gly Gly Leu Gly Gly Leu Gly Gly Gly Leu Gly Gly Leu Gly Gly
                260                 265                 270

Leu Gly Gly Leu Gly Gly Tyr Gly Gly Ser Ala Ala Ala Ala Ala
            275                 280                 285

Ala Ala Ala Ala Ala Ala Gly Gly Gly Leu Gly Gly Val Gly Phe
        290                 295                 300

Tyr Gly Gly Arg Gly Gly Arg Arg Gly Arg Gly Arg Gly Gly Arg Arg
305                 310                 315                 320

Arg Ala Ala Ala Ala Ala Ala Ala Ala Ala Ala Ala Gly Gly
            325                 330                 335

Gly Gly Gly Gly Gly Gly Gly Gly Gly Gly Gly Gly Ala Gly Ala
            340                 345                 350

Ala Ala Ala Ala Ala Ala Ala Ala Ser Ala Ser Ala Ser Arg Gln
            355                 360                 365

Met Ser Gly Ile Arg Asp Ala Leu Gly Asp Ile Lys Asp Leu Leu Arg
    370                 375                 380

Ser Asn Gly Ala Ser Ala Lys Ala Ser Ala Lys Ala Ser Ala Val Ala
385                 390                 395                 400

Ser Thr Lys Ser Gln Ile Asp Asp Leu Lys Asp Val Leu Lys Asp Leu
            405                 410                 415

Ala Gly Leu Leu Lys Ser Ser Ala Ser Ala Ser Ala Ser Ala Ser Ala
```

```
                     420             425             430
Ser Ala Ser Ala Gly Gly Gly Gly Gly Gly Asn Gly Gly Asn
            435             440             445
Gly Gly Gly Gly Gly Gly Gly Ala Gly Ala Leu Ala Ala Leu Ala
    450             455             460
Ala Ala Gly Ala Gly Gly Gly Leu Gly Gly Gly Gly Gly Gly Ala
465             470             475             480
Leu Ala Ala Ala Leu Ala Ala Ala Gly Ala Gly Gly Gly Phe Gly
                485             490             495
Gly Leu Gly Gly Leu Gly Gly Leu Gly Gly Gly Ser Ala Ala Ala
            500             505             510
Ala Ala Ala Ala Ala Ala Ser Gly Gly Gly Arg Ala Leu Arg
            515             520             525
Arg Ala Leu Arg Arg Gln Met Arg Gly Gly Ser Ala Ala Ala
    530             535             540
Ala Ala Ala Ala Ala Ala Ala Gly Gly Gly Trp Gly Gly Met
545             550             555             560
Gly Gly Gly Phe Gly Val Gly Leu Gly Gly Phe Gly Gly Phe
                565             570             575
Gly Gly Gly Ser Ser Ala Ala Ala Ala Ala Ala Ala Ala Ala
            580             585             590
Gly Phe Gly Gly Gly Gly Arg Arg Gly Arg Gly Arg Gly Arg Gly Gly
            595             600             605
Asp Gly Asp Gly Asn Gly Ala Ser Ala Val Ala Ala Ala Ala Ala
        610             615             620
Ala Ala Ala Ala Gly Gly Ser Ala Ala Asp Val Ala Ala Ala Ala
625             630             635             640
Ala Ala Ala Ala Met Tyr Gly Asp Gly Ala Asp Gly Pro Asp Phe Asp
            645             650             655
Asn Gly Phe Gly Gly Gly Asn Gly Asn Gly Gly Gly Ser Gly Gly
                660             665             670
Gly Gly Ser Gly Gly Gly Gly Ser Gly Gly Gly Ser Gly Gly Gly
            675             680             685
Gly Ser Gly Gly Ser Gly Gly Gly Gly Ser Gly Gly Ser Gly Gly
        690             695             700
Gly Gly Ser Gly Gly Gly Gly Asn Asn Gly Trp Gly Asn Asn Gly Asn
705             710             715             720
Asn Lys Tyr Asp Asp Asp Asp Cys Asp Glu Tyr Gly Asn Pro Ile Arg
                725             730             735
Arg Gly (2) INFORMATION FOR SEQ ID NO: 4:

(i) SEQUENCE CHARACTERISTICS:
        (A) LENGTH: 3331
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Pinctada fucata
        (G) CELL TYPE: mantle epithelial cell (ix) FEATURE:
        (A) NAME/KEY: CDS
        (B) LOCATION: from 50 to 2263
        (C) IDENTIFICATION METHOD: P (by similarity to some other
``` pattern)

(xi) SEQUENCE DESCRIPTION: SEQ ID NO:4:

```
TCGGATCTCC CCACACAACA TAGATAGAGG ATATCCGCCT GGGTTCACA             49

ATG AAG TTA CTG GTG GTT CTC ACC ACC CTC GTG GGC TTT AGC TCA GCA   97
Met Lys Leu Leu Val Val Leu Thr Thr Leu Val Gly Phe Ser Ser Ala
 1               5                  10                  15

CTA AGT TTC GGT TGT AAT TAC AGA CCA GTA TTA GGC TTC AAT TCA CAG  145
Leu Ser Phe Gly Cys Asn Tyr Arg Pro Val Leu Gly Phe Asn Ser Gln
            20                  25                  30

TAT ATG CTG GGA GGA CTA AGA CTT TTC TGT ATG CCT GCC ATG GTT TAT  193
Tyr Met Leu Gly Gly Leu Arg Leu Phe Cys Met Pro Ala Met Val Tyr
        35                  40                  45

GAT CCA TGG GCA TGT GGT TGC GTT TCG GCA TGG AGC AGT GCA GGT CTT  241
Asp Pro Trp Ala Cys Gly Cys Val Ser Ala Trp Ser Ser Ala Gly Leu
    50                  55                  60

TAC GGT GTC GGA GGG GGC GGA GGC GCC TGG GGA GCT GGC GGT GCT GGA  289
Tyr Gly Val Gly Gly Gly Gly Ala Trp Gly Ala Gly Gly Ala Gly
 65                  70                  75                  80

GGA GCC GAC GGC GGA CGC GGC GGC GGC GGT GGA GAT TGG GAA TAT GAC  337
Gly Ala Asp Gly Gly Arg Gly Gly Gly Gly Asp Trp Glu Tyr Asp
                85                  90                  95

TAT GAT GAC GAC AGC GAT GAC GAT GAT GAA TGG GAC TGG GAT GAT GAC  385
Tyr Asp Asp Asp Ser Asp Asp Asp Asp Glu Trp Asp Trp Asp Asp Asp
                    100                 105                 110

GGT GGA ATG GGA GCT GGC GCC GGA GGT GGT GCT GGT GGT GGT GCC GGA  433
Gly Gly Met Gly Ala Gly Ala Gly Gly Ala Gly Gly Gly Ala Gly
            115                 120                 125

GGT GGT GCT GGT GCT GGT GCT GGA GCA GGC GCA GGA GCA GGA GCA GGT  481
Gly Gly Ala Gly Ala Gly Ala Gly Ala Gly Ala Gly Ala Gly Ala Gly
        130                 135                 140

GCT GGA CTC GGA CTT GGA TTG GGC GGA GGT CTC GGA GGT GGA CTT GGC  529
Ala Gly Leu Gly Leu Gly Leu Gly Gly Gly Leu Gly Gly Gly Leu Gly
145                 150                 155                 160

GGA CTT GGA GGT CTT GGC GGA CTT GGC GGT GGA GAC GAT TTA TTT GAT  577
Gly Leu Gly Gly Leu Gly Gly Leu Gly Gly Gly Asp Asp Leu Phe Asp
                165                 170                 175

TTA GAT TTC GAT GAT CTT GGT GCA GCT CTT GCC CTC GGT GGA GCT GGT  625
Leu Asp Phe Asp Asp Leu Gly Ala Ala Leu Ala Leu Gly Gly Ala Gly
            180                 185                 190

GGA GCT GGA GGT GCT GCT GCT GCT GCT GCA GCT GCC GCT GCT GCC GCC  673
Gly Ala Gly Gly Ala Ala Ala Ala Ala Ala Ala Ala Ala Ala Ala
        195                 200                 205

GGG GGT GGA GTT GGT GGA GCT GCT GCC GCA GCC GCA GCC GCT GCT GCC  721
Gly Gly Gly Val Gly Gly Ala Ala Ala Ala Ala Ala Ala Ala Ala
210                 215                 220

GCT GCA GGA GGA GGC GCA GGT AGA CTT GGA GGA GCT GCT GCT GCA GCC  769
Ala Ala Gly Gly Gly Ala Gly Arg Leu Gly Gly Ala Ala Ala Ala Ala
225                 230                 235                 240

GCA GCC GCT GCT GCC GCT GCA GGA GGC GCA GGT GGA CTT GGA GGA CTC  817
Ala Ala Ala Ala Ala Ala Ala Gly Gly Ala Gly Gly Leu Gly Gly Leu
                245                 250                 255

GGT GGC GGA CTT GGA GGA CTC GGT GGC GGA CTT GGA GGC CTC GGA GGT  865
Gly Gly Gly Leu Gly Gly Leu Gly Gly Gly Leu Gly Gly Leu Gly Gly
            260                 265                 270

CTT GGT GGC CTC GGA GGA TAT GGA GGA TCT GCT GCT GCC GCT GCT GCT  913
Leu Gly Gly Leu Gly Gly Tyr Gly Gly Ser Ala Ala Ala Ala Ala Ala
        275                 280                 285

GCT GCC GCC GCT GCT GCC GGA GGT GGA GGA CTC GGT GGT GTT GGT TTC  961
Ala Ala Ala Ala Ala Ala Gly Gly Gly Gly Leu Gly Gly Val Gly Phe
```

-continued

|  |  |
|---|---|
| TAC GGT GGA CGA GGA GGT AGA CGC GGT CGA GGA AGA GGA GGC CGC AGA<br>Tyr Gly Gly Arg Gly Gly Arg Arg Gly Arg Gly Arg Gly Gly Arg Arg<br>305    310    315    320 | 1009 |
| CGT GCT GCT GCT GCC GCT GCT GCA GCT GCC GCC GCA GCC GCT GGT GGT<br>Arg Ala Ala Ala Ala Ala Ala Ala Ala Ala Ala Ala Ala Ala Gly Gly<br>    325    330    335 | 1057 |
| GGC GGA GGA GGT GGA GGT GGT GGA GGA GGA GGC GGA GGC GCT GGT GCT<br>Gly Gly Gly Gly Gly Gly Gly Gly Gly Gly Gly Gly Gly Ala Gly Ala<br>    340    345    350 | 1105 |
| GCC GCT GCC GCT GCA GCC GCT GCT GCA TCT GCT TCA GCT TCT AGA CAA<br>Ala Ala Ala Ala Ala Ala Ala Ala Ala Ser Ala Ser Ala Ser Arg Gln<br>    355    360    365 | 1153 |
| ATG AGT GGT ATA AGG GAC GCA TTA GGA GAC ATT AAA GAC CTT CTC AGG<br>Met Ser Gly Ile Arg Asp Ala Leu Gly Asp Ile Lys Asp Leu Leu Arg<br>  370    375    380 | 1201 |
| AGT AAT GGA GCC TCT GCA AAA GCC TCT GCT AAA GCA TCA GCA GTA GCA<br>Ser Asn Gly Ala Ser Ala Lys Ala Ser Ala Lys Ala Ser Ala Val Ala<br>385    390    395    400 | 1249 |
| AGC ACA AAA TCT CAA ATT GAC GAT TTG AAG GAT GTC TTA AAG GAT CTT<br>Ser Thr Lys Ser Gln Ile Asp Asp Leu Lys Asp Val Leu Lys Asp Leu<br>    405    410    415 | 1297 |
| GCA GGT CTA TTG AAA AGC TCA GCA TCT GCT TCA GCA TCT GCA TCT GCA<br>Ala Gly Leu Leu Lys Ser Ser Ala Ser Ala Ser Ala Ser Ala Ser Ala<br>    420    425    430 | 1345 |
| TCA GCT TCA GCT GGA GGT GGA GGC GGT GGT GGT AAC GGA GGT GGT AAC<br>Ser Ala Ser Ala Gly Gly Gly Gly Gly Gly Gly Asn Gly Gly Gly Asn<br>    435    440    445 | 1393 |
| GGA GGA GGA GGC GGC GGT GGA GCT GGA GCT CTA GCT GCT GCT CTC GCT<br>Gly Gly Gly Gly Gly Gly Gly Ala Gly Ala Leu Ala Ala Ala Leu Ala<br>  450    455    460 | 1441 |
| GCT GCA GGA GCC GGA GGT GGA CTT GGA GGT GGA GGC GGA GGC GGA GCT<br>Ala Ala Gly Ala Gly Gly Gly Leu Gly Gly Gly Gly Gly Gly Gly Ala<br>465    470    475    480 | 1489 |
| TTA GCC GCT GCA CTA GCT GCT GCT GGT GCA GGT GGA GGA GGT TTT GGT<br>Leu Ala Ala Ala Leu Ala Ala Ala Gly Ala Gly Gly Gly Gly Phe Gly<br>    485    490    495 | 1537 |
| GGA CTT GGA GGA CTA GGC GGT CTT GGT GGG GGA TCT GCC GCA GCT GCT<br>Gly Leu Gly Gly Leu Gly Gly Leu Gly Gly Gly Ser Ala Ala Ala Ala<br>    500    505    510 | 1585 |
| GCA GCC GCT GCC GCT GCT GCA TCA GGT GGT GGA GGA AGA GCA CTT AGA<br>Ala Ala Ala Ala Ala Ala Ala Ser Gly Gly Gly Gly Arg Ala Leu Arg<br>    515    520    525 | 1633 |
| AGG GCT TTG AGA AGA CAA ATG CGT GGA GGT GGA TCC GCT GCT GCC GCT<br>Arg Ala Leu Arg Arg Gln Met Arg Gly Gly Gly Ser Ala Ala Ala Ala<br>  530    535    540 | 1681 |
| GCT GCT GCT GCT GCA GCT GCT GCT GGA GGT GGA TGG GGA GGT GGA ATG<br>Ala Ala Ala Ala Ala Ala Ala Ala Gly Gly Gly Trp Gly Gly Gly Met<br>545    550    555    560 | 1729 |
| GGT GGA GGA TTC GGA GTA GGT CTC GGT GGA GGA TTC GGA GGA GGA TTT<br>Gly Gly Gly Phe Gly Val Gly Leu Gly Gly Gly Phe Gly Gly Gly Phe<br>    565    570    575 | 1777 |
| GGT GGT GGA TCA TCA GCA GCA GCT GCT GCC GCT GCT GCA GCC GCC GCT<br>Gly Gly Gly Ser Ser Ala Ala Ala Ala Ala Ala Ala Ala Ala Ala Ala<br>    580    585    590 | 1825 |
| GGA TTT GGT GGA GGT GGA CGA AGA GGT AGA GGT AGA GGA CGT GGA GGC<br>Gly Phe Gly Gly Gly Gly Arg Arg Gly Arg Gly Arg Gly Arg Gly Gly<br>    595    600    605 | 1873 |
| GAT GGC GAC GGT AAC GGA GCT AGT GCT GTA GCT GCA GCC GCC GCC GCT<br>Asp Gly Asp Gly Asn Gly Ala Ser Ala Val Ala Ala Ala Ala Ala Ala | 1921 |

```
       610                 615                 620
GCT GCT GCT GCT GGA GGA TCT GCT GCT GAT GTT GCC GCT GCC GCT GCT   1969
Ala Ala Ala Ala Gly Gly Ser Ala Ala Asp Val Ala Ala Ala Ala Ala
625                 630                 635                 640

GCA GCC GCA GCT ATG TAC GGT GAC GGT GCT GAT GGA CCT GAT TTC GAT   2017
Ala Ala Ala Ala Met Tyr Gly Asp Gly Ala Asp Gly Pro Asp Phe Asp
                645                 650                 655

AAT GGA TTC GGT GGT GGA AAC GGA AAT GGA GGT GGC GGA TCT GGT GGT   2065
Asn Gly Phe Gly Gly Gly Asn Gly Asn Gly Gly Gly Gly Ser Gly Gly
                660                 665                 670

GGC GGA TCC GGC GGA GGT GGA TCC GGT GGC GGA TCT GGA GGT GGC GGT   2113
Gly Gly Ser Gly Gly Gly Gly Ser Gly Gly Gly Ser Gly Gly Gly Gly
                675                 680                 685

GGA TCT GGT GGA TCA GGC GGT GGC GGC GGA TCT GGT GGT TCA GGC GGT   2161
Gly Ser Gly Gly Ser Gly Gly Gly Gly Gly Ser Gly Gly Ser Gly Gly
            690                 695                 700

GGC GGA TCA GGC GGC GGT GGA AAC AAT GGA TGG GGA AAT AAC GGC AAC   2209
Gly Gly Ser Gly Gly Gly Gly Asn Asn Gly Trp Gly Asn Asn Gly Asn
705                 710                 715                 720

AAT AAA TAT GAC GAT GAT GAC TGT GAT GAA TAT GGT AAC CCT ATT AGA   2257
Asn Lys Tyr Asp Asp Asp Asp Cys Asp Glu Tyr Gly Asn Pro Ile Arg
                725                 730                 735

AGG GGG                                                           2263
Arg Gly

TAAATTATTT GACATTATCC GCCATTTGAC TCATTTTTCT TAGTTCTCTA TGTTTTATAC  2323

TTCACCTTAG ATTGTTTTAG TTTGATTGAA TAAATTATGT TTTCGATATA AATTTTTTTT  2383

AAATTAAATT AAACTTTATT AGTTGACCTG TAAACTTTTT CATGGAGTTA TAATCTAAGG  2443

AACAAAAAAC ATACATAATA TGTTCAGTAT TGTGGTAAAG CACCTGTACC GCAAACACAA  2503

TCACCTCTAT ACATGTATAC AAAATCAGTA ATGCTGACAA AATCTTCTAC ACTCTCACCT  2563

ACACACTCGC ACACAGTCCT CTTACATACA CAGCACTATA ATATCCTGAA CATGAAGTTT  2623

GTGTTGATAA AAAGTTCAGA AAAATCTCCC CTACATCACC TGATCTTTCA CTGAAAATTT  2683

ACGACAAGTA TTGAAAATAG CAGAAAGAAA ACGGGAAATT GAGAAGTTTT CTATAAAAAA  2743

CAATCGGAAC AATGACTGGA ATGACAAGGA TGAAATAAT GATAACTTAC ATTAATTAAG   2803

GCCCCAATAA TCTCTCTATT TTCAAACTTT TTTTTCAAAT GTTCTCTCTA ACTCACTTGC  2863

ATCTATGTGG AAATTCACAT ACTATACTAA ATTACCACAA GTATCAAGGT TTCACAACCT  2923

CTCATGCCTT CATGGCAGAC CATGCTGGGT ATTTGTCTAA CAATGCCTCA TAAATACATA  2983

AAACTAACTA ACAAAATAGG TCAGTCTGTA ACAAATTATT AATGCACCAT TATTGCATTT  3043

TCTAAAACAA AGCATACACT GGATATTGGC AGACAAAATG TTGTTATTGG ATACCTTTCC  3103

ATTCTATCTA GACACTTGCT TTCCACAAGT CATCATAAAT AAATCCCCCC TATCCCAAAT  3163

GTCAATGGAA TGCCCCAACC CTTCCCCCAT AATTTTAAAA CCTAGAATAA ATTAAAACAT  3223

CTATAGTTCG TCATGATCAT CTTTCTTATC ATCCTCTTCT TCTTCCTCCT CCTCCTTCTT  3283

CTTCTTCCTC CTCCTCAGGT TCTTGGCTGC CTGCTCCTTC CTTGCCAA              3331
```